United States Patent
Nguyen et al.

(10) Patent No.: US 9,956,141 B2
(45) Date of Patent: May 1, 2018

(54) AUTOMATIC FLUID CONTAINER SWITCHING IN A BLOOD PROCESSING SYSTEM

(75) Inventors: Lan Nguyen, Vernon Hills, IL (US); John Foley, Wheeling, IL (US); Jonathan Prendergast, Palatine, IL (US); Brian Case, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 720 days.

(21) Appl. No.: 13/604,133

(22) Filed: Sep. 5, 2012

(65) Prior Publication Data
US 2013/0233394 A1 Sep. 12, 2013

Related U.S. Application Data

(60) Provisional application No. 61/531,305, filed on Sep. 6, 2011.

(51) Int. Cl.
*A61J 1/20* (2006.01)
*A61M 1/34* (2006.01)

(52) U.S. Cl.
CPC .............. *A61J 1/20* (2013.01); *A61M 1/3496* (2013.01); *A61M 1/342* (2013.01); *A61M 2205/3393* (2013.01); *A61M 2205/505* (2013.01); *Y10T 137/0324* (2015.04); *Y10T 137/27* (2015.04); *Y10T 137/7313* (2015.04)

(58) Field of Classification Search
CPC .... A61J 1/20; Y10T 137/27; Y10T 137/0324; Y10T 137/7313; A61M 2205/3393
USPC .................................................. 222/58; 137/2
See application file for complete search history.

(56) References Cited

U.S. PATENT DOCUMENTS

| | | | |
|---|---|---|---|
| 4,646,784 A | 3/1987 | de Leeuwe | |
| 4,650,464 A * | 3/1987 | Ruiz | A61M 5/172 128/DIG. 13 |
| 4,778,450 A | 10/1988 | Kamen | |
| 6,466,879 B1 * | 10/2002 | Cantu | A61M 1/3672 210/782 |
| 6,581,801 B2 | 6/2003 | Gauthier | |
| 6,675,643 B2 * | 1/2004 | Weissmann | G01F 17/00 73/149 |
| 7,206,715 B2 * | 4/2007 | Vanderveen | A61M 5/1684 702/127 |
| 9,144,644 B2 * | 9/2015 | Hungerford | A61M 5/14228 |
| 2003/0176833 A1 * | 9/2003 | Libermann | A61M 3/0241 604/65 |
| 2004/0078152 A1 * | 4/2004 | Rameau | G01F 23/205 702/55 |
| 2009/0151474 A1 * | 6/2009 | Mehus | G01G 3/14 73/862.52 |
| 2009/0212070 A1 * | 8/2009 | Johnson | A61M 1/36 222/58 |

(Continued)

*Primary Examiner* — Alexander Satanovsky
*Assistant Examiner* — Lina Cordero
(74) *Attorney, Agent, or Firm* — Cook Alex Ltd.

(57) ABSTRACT

Systems and methods for determining when a fluid supply container of a blood processing apparatus becomes empty. The system uses a scale to monitor and detect when a fluid supply container is empty based on the rate of change of the container weight and whether the container weight is below a pre-established threshold, and a controller receives a signal from the scale and controls the operation of a pump to stop pumping when the fluid supply container is empty.

11 Claims, 3 Drawing Sheets

(56) References Cited

U.S. PATENT DOCUMENTS

2011/0064612 A1* 3/2011 Franzoni ............... A61M 1/342
422/44

* cited by examiner

AUTOMATIC FLUID CONTAINER SWITCHING IN A BLOOD PROCESSING SYSTEM

CROSS REFERENCE TO RELATED APPLICATION

This application claims the benefit of the filing date of U.S. Provisional Application Ser. No. 61/531,305, filed Sep. 6, 2011, the entire contents of which is incorporated by reference herein.

FIELD OF THE INVENTION

The present disclosure relates generally to methods and apparatus for monitoring and detecting empty fluid containers, and more particularly, to methods and apparatus for monitoring and detecting empty fluid containers used with a blood processing or apheresis instrument.

BACKGROUND OF THE INVENTION

Often, a blood processing or apheresis instrument is used to separate blood components from whole blood. Such instruments, also known as "separators", typically separate a selected blood component(s) from whole blood by passing the blood of a donor through the instrument to separate one or more blood components from the whole blood under the influence of centrifugal force or other means for effecting separation. The remainder of the whole blood is then returned to the circulatory system of the donor. It is, therefore, an extracorporeal blood component collection process. Apheresis instruments are commercially available from various sources, including the Amicus® Separator which is available from Fenwal Inc., of Lake Zurich, Ill.

Instruments such as the Amicus Separator may utilize a single-use apheresis kit for collection of a desired blood component. The instrument may have pumps, clamps, and valves that move and direct donor blood through the kit. Such single-use kits are often referred to as "disposables". Connected to such a kit may be one or more fluid supply containers of replacement fluids for infusion into the donor. A therapeutic plasma exchange (TPE) procedure may require multiple containers of fluid, typically albumin or fresh frozen plasma, to replace potentially up to three or more liters of the patient's waste plasma.

During an apheresis procedure, one of the most significant concerns is prevention of an air embolism. To reduce the risk of air embolism, it is vital to ensure that air does not enter the apheresis disposable kit during a blood component collection procedure. For example, air can be drawn into the disposable kit during a collection procedure when the fluid source, or fluid supply container attached to the kit becomes exhausted of fluid.

During therapeutic apheresis procedures, a patient's particular blood component of interest, such as plasma, is continuously removed while a replacement fluid, which in the case of plasmapheresis is normal plasma or albumin, is continuously infused. In current practice, two replacement fluid supply containers are usually connected to the disposable kit. Replacement fluid is drawn from one container while the other container is clamped. The operator must closely monitor the fluid level in the "active" container. When this container empties, the operator must close its clamp while opening the clamp on the other container. If the operator is occupied with the patient, or otherwise distracted, and does not perform this operation, a large volume of air may be drawn into the disposable kit, requiring air to be purged.

Apheresis instruments are typically equipped with air detection systems that continually monitor the fluid that is being returned to the donor/patient. If, during a procedure, air reaches the air detection system, blood processing is interrupted until the air is purged from the system. Often multiple air purges are required to clear this air. Since blood is not being processed during these purges, the overall procedural efficiency of the blood collection procedure is decreased.

It is known to provide an apparatus and methods for automatically determining when a fluid container becomes empty and to terminate further use of the empty container. It is further known to provide an apparatus and methods for determining when a fluid container becomes empty independent of the size, volume or composition of matter of the container and to switch to a full container if available. See U.S. Patent Application Publication No. 2009/0212070, which is incorporated herein by reference in its entirety. While such an apparatus and method is an improvement over prior apparatus and methods, stopping and or switching fluid flow may occur even though the fluid container is not empty, but merely has a slow flow rate due to, e.g. the viscosity of the fluid being high, a poor spike connection with the fluid container, or other reasons.

Accordingly, it would be desirable to provide an apparatus and system and/or method that is less likely to terminate further use of a fluid container when the container is not empty and avoid such "false switches." It would also be desirable to provide a system that alerts the operator of: a low weight on both replacement fluid containers; a low weight in the "second" container (i.e., the container that is to be switched to) which may be an indication that no such "second" container is present; and a low flow from a "current" container that would cause a switch when switching from the previous container occurred in less than a predetermined time.

SUMMARY

In one aspect, the present disclosure is directed to a system for determining when a fluid supply container of a fluid processing apparatus is empty. The system includes a first fluid supply container and a first scale for measuring the weight of the first supply container. The scale provides an output signal that indicates the measured weight. The system also includes a pump for pumping fluid from the first supply container. The system further includes a controller that determines the rate of change in the weight of the first container and also when the weight of the first fluid supply container is below a first pre-established threshold.

In another aspect, the present disclosure is directed to a method of determining when a fluid supply container of a fluid processing system is empty. The method includes providing a first fluid supply container, monitoring the weight of the first fluid supply container while fluid is being dispensed therefrom, establishing a first threshold weight for the first fluid supply container and determining a rate of change of the weight of the container. The method further includes determining when the rate of change of the weight of the first container becomes substantially zero and the weight of the container is less than the threshold weight. The method also includes stopping the operation of a fluid pump associated with the container after determining the conditions described above.

Other aspects of the systems and methods of the present disclosure are set forth below.

BRIEF DESCRIPTION OF THE DRAWINGS

This disclosure may best be understood by reference to the following description taken in conjunction with the accompanying drawings, in which like reference numerals identify like elements in the figures, and in which.

DESCRIPTION OF THE PREFERRED EMBODIMENTS

Figure 1:
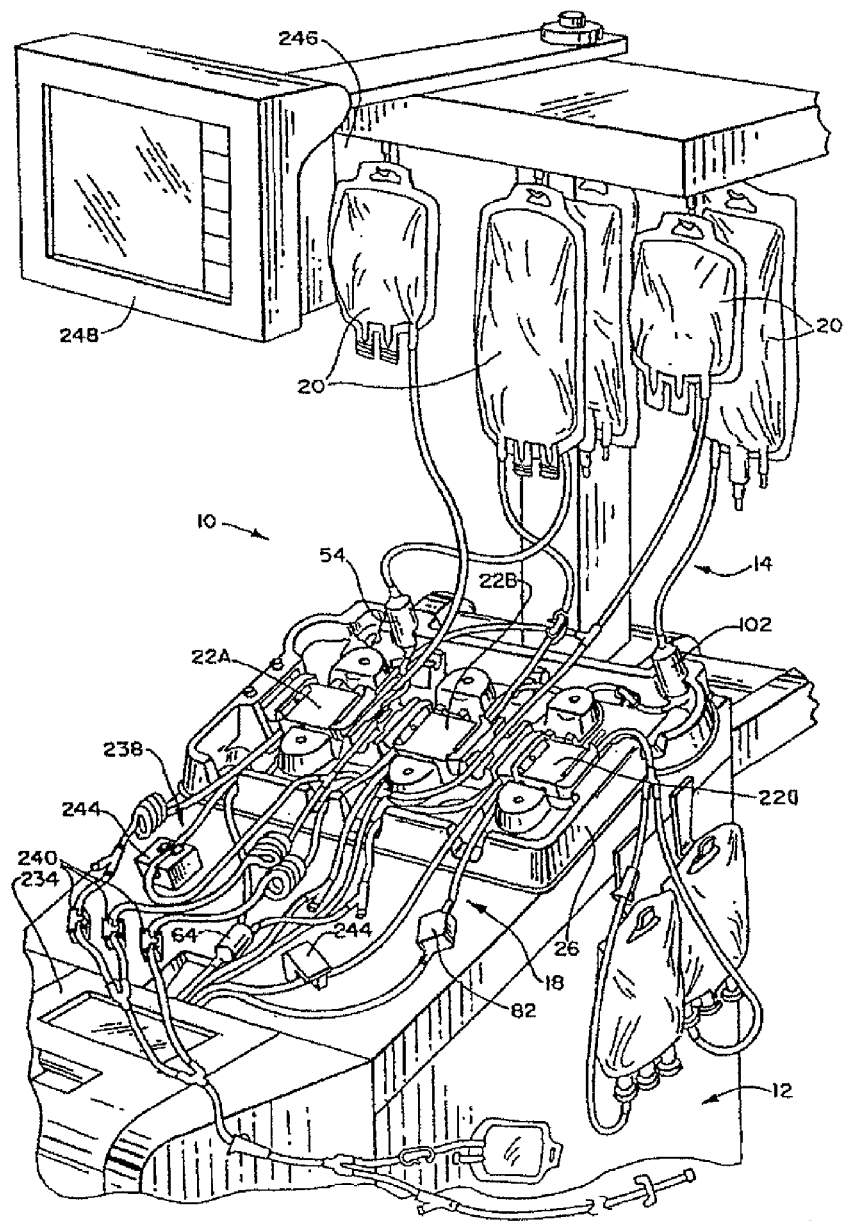
FIG. 1 is a perspective view of a blood processing system with a plurality of containers hanging therefrom.

The present disclosure is directed to apparatus systems and methods of using weight scales, a pump and a controller to detect, as quickly as possible, an empty fluid supply container. The apparatus identifies the time at which the weight of the container is less than a pre-established threshold and the rate of change of the weight of the container is less than expected based on a known pump rate. The pump that is drawing fluid from the now empty fluid container is then commanded to stop pumping from the container before air enters a blood collection kit. If using two fluid supply containers, the apparatus can be made to automatically start pumping from the second container when it determines that the first container is empty and also determines that there is a non-empty container available. By analyzing both the weight of the container and the rate of change of the weight of the container, the system can recognize and differentiate between a condition where the supply container is, in fact, empty and a condition where the supply container is not yet empty.

The system also preferably notifies the operator if the system detects a low flow scenario within a predetermined time after a switch of pumping from a first container to pumping from a second container, or a low weight is detected on one or both of the scales for the fluid containers. This may include a scenario where a second supply container has not been loaded or is otherwise missing.

The apparatus and methods of the present disclosure also more accurately track an accumulated volume of fluid pumped from the first and second fluid supply containers based on the weight of the containers, and adjusts the accumulated volume by an appropriate amount for each time pumping switches between the containers in response to a determination that a container is empty. This is to account for the volume of replacement fluid in the tubing segment leading to the valve(s) that is not otherwise accounted for in the weight of the container.

The improved monitoring of empty fluid supply containers with the present methods and apparatus keeps air from being pumped into the blood collection kit from an empty container and substantially decreases the need to perform air purges. Thus, procedural efficiency is increased. The automatic switching between two replacement fluid supply containers during therapeutic apheresis, also allows the operator to concentrate on the patient and not the amount of fluid remaining in the container that is in use.

It will be understood that the present methods and apparatus may be embodied in other specific forms without departing from the spirit of the disclosure. The present examples and embodiments, therefore, are to be considered in all respects as illustrative and not restrictive, and the scope of the disclosure is not to be limited to the details presented herein.

The apparatus of the present disclosure detects an empty fluid supply container and/or the need to switch to a non-empty replacement fluid supply container by continuously analyzing its change in weight over short intervals and weighing the fluid supply container to determine whether its weight is below a pre-established threshold weight. Thus, it can accurately detect the presence of an empty container and, if appropriate, switch to a replacement fluid container.

FIG. 1 shows a blood processing system 10, which is particularly well-suited for processing whole blood. A number of containers 20 are suspended on hangers on the system 10. Some of the containers 20 may be fluid supply containers that dispense liquids to a blood donor during a blood collection procedure or a therapeutic apheresis procedure in accordance with the methods and systems described herein.

Figure 2:
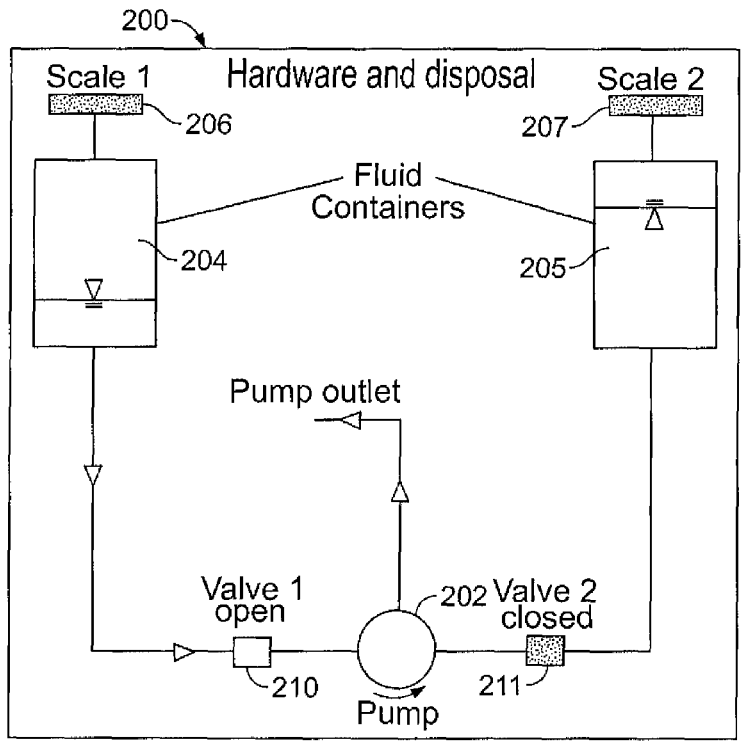
FIG. 2 is a diagram of a pumping system for two of the containers shown in FIG. 1 in accordance with the present disclosure.
Figure 3A:
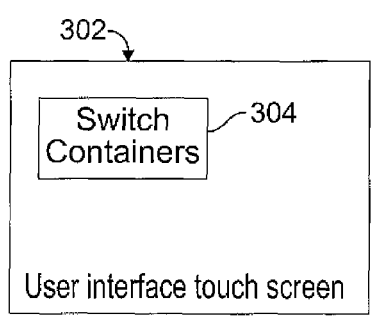
FIG. 3A is a diagrammatic view of a user interface touch screen for controlling the pumping system shown in FIG. 2.
Figure 3B:
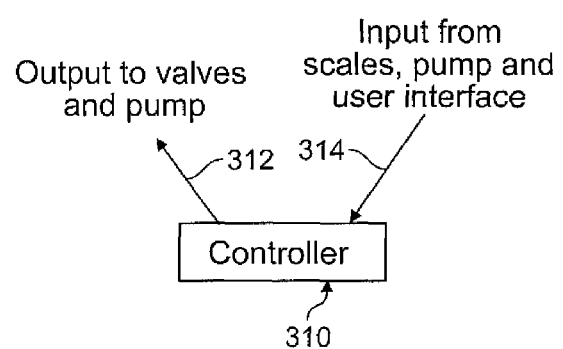
FIG. 3B is a diagrammatic view of a controller for the pumping system in FIG. 2.

FIG. 2 illustrates a monitoring system, generally designated 200, in accordance with the present disclosure. In the example of FIG. 2, a pump 202 is turning in a counterclockwise direction and fluid is drawn from a first fluid supply container 204 which is suspended from a first scale 206 and through a first valve 210 that is in an open condition. If the operator uses a user interface touch screen 302 in FIG. 3A, such as by touching a "Switch Containers" button or field 304, a controller 310 in FIG. 3B receives a signal on controller input line 314 and sends a signal via an output line 312 to command the pump 202 to stop turning, i.e., to stop pumping. A second valve 211, which was initially in a closed condition, is then opened, and the first valve 210, which was initially open, is then closed. The controller 310 then commands the pump 202 to turn in a clockwise direction to draw fluid from the second fluid supply container 205 which is suspended from the second scale 207. In accordance with the present disclosure, if the operator does not touch the "Switch Containers" button or field 304 and the first fluid supply container 204 on the first scale 206 empties, the controller 310 will automatically detect the empty container and perform the operation to switch from which container the pump is drawing fluid.

Figure 4:
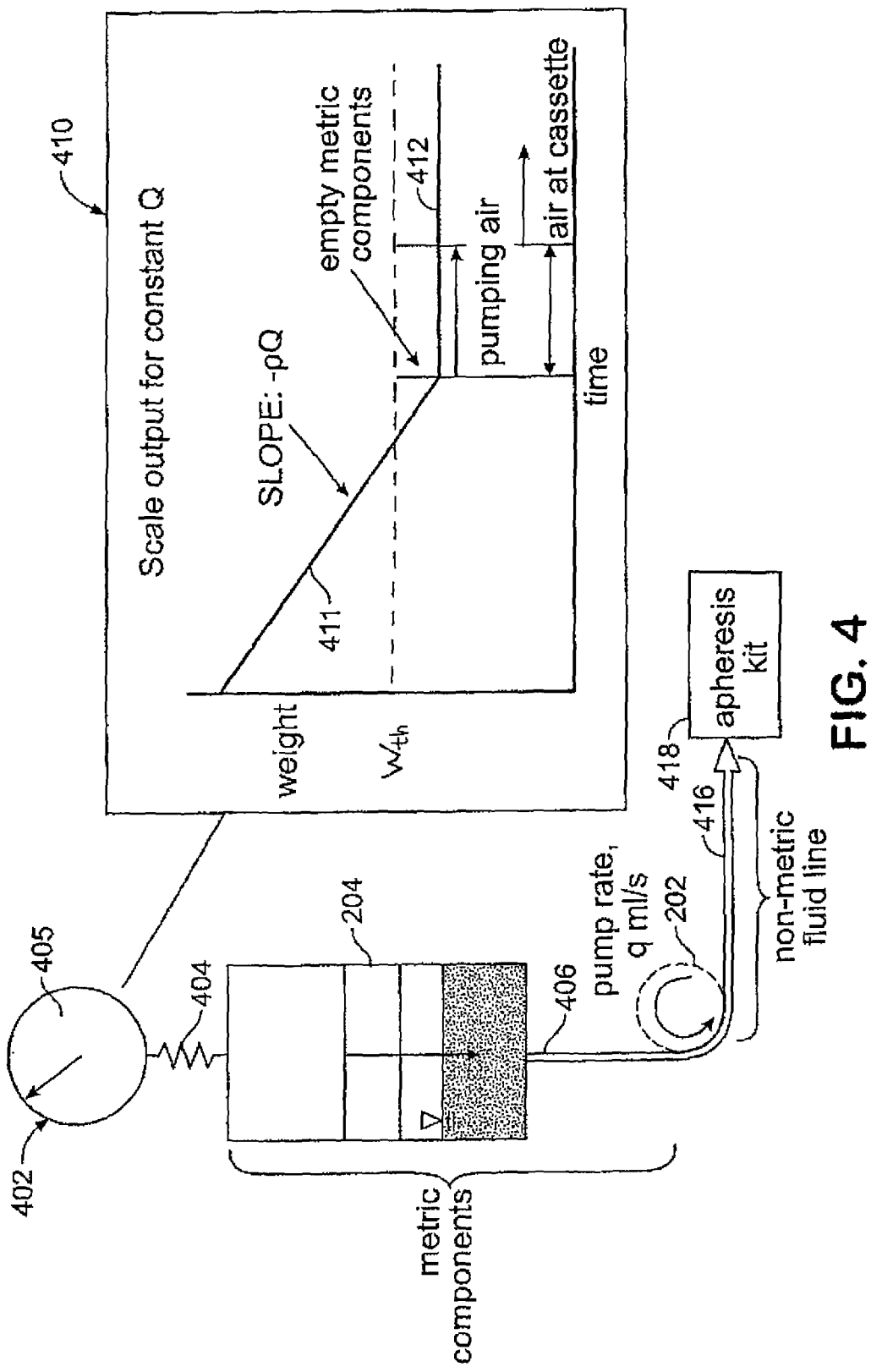
FIG. 4 is a diagrammatic view of the control of the pump in FIG. 2 by means of monitoring the rate of change of the weight of a container as it is being emptied by the pump.

FIG. 4 illustrates the control of the pump 202 in FIG. 2 by means of monitoring the rate of change of the weight of a container as it is being emptied by the pump as well as the instantaneous weight of the container. A scale 402, represented by a spring 404 and a dial 405, is used by the controller 310 to continuously monitor the weight of the metric components. The metric components include the fluid within the first fluid supply container 204, the first container 204 itself, the tubing 406, and possibly a spike and/or drip chamber (not shown) that may be suspended from the scale 402. The system also includes non-metric components, such as the replacement fluid line 416, and perhaps a filter and/or reservoir (not shown), that do not hang from the scale, and which lead to the disposable kit 418.

When the pump 202 causes fluid to be dispensed from the first fluid supply container 204 at a rate of Q milliliters each second, the output weight indicated by the scale 402 continuously changes with time as shown by an angular line portion 411 of graph 410. When the metric components are empty, the weight determined by the scale 402 "flat lines," i.e. stops changing, as indicated by the horizontal line portion 412 of graph 410. When the procedure reaches the horizontal line portion 412 of graph 410, air will be drawn into the non-metric fluid line 416. Thus, it is important to recognize when the "flat line" 412 begins. Unfortunately, noise in the output signal of the scale 402 may make it impossible to determine from the scale data alone the exact time at which the rate of change in the weight becomes zero, especially at low flow rates.

Preferably, to overcome this noise issue, the controller 310 (FIG. 3B) may monitor both the weight reading that is output from the scale 402, and the volume of fluid delivered by the pump 202 over a predefined, pump-volume dependent period, or pump-unit interval. During every pump-unit interval, the controller 310 compares the scale's weight change over the pre-defined period to the volume pumped during that period. If the ratio of the two values (weight change divided by pump volume) is less than a predetermined value for two consecutive intervals, one of the two criteria for determining that the fluid supply container is empty is satisfied. It should be appreciated that the ratio of the two values when the fluid supply container is not empty should be one (i.e., 1:1). When the fluid supply container is empty, the ratio should be zero. If the ratio of the two values is somewhere in between 0 and 1, one of the two criteria for determining that the fluid supply container is empty is satisfied. Thus, in one non-limiting example of a therapeutic plasma exchange procedure, if the ratio of the two values is less than about 0.375 for two consecutive intervals, one of the two criteria for determining that the fluid supply container is empty is satisfied. Use of an intermediate value assists in minimizing any false determinations due to noise.

To avoid pumping air into the disposable kit 418, the scale flat line must be identified and the pump 202 stopped before the pump 202 can move fluid the full length of the non-metric portion of the replacement fluid line 416. Given a fluid line 416 length L (in inches) that is V milliliters/inch (ml/in) in volume, and a pump rate of q milliliters/second (ml/s), the maximum response time must be tr=LV/q seconds. If the scale has a minimum resolution of w grams (g), then the weight monitoring of the scale output must allow for a weight change of at least w. Given the replacement fluid density ρ grams/milliliter (g/ml) and a pump rate of q ml/s, the minimum detection period is td=w/(ρ*q) seconds. Accordingly, to insure that air will not be pumped past the disposable kit 418, the ratio tr/td (response time available to response time required) must be greater than 1, i.e., LV/q÷w/(ρ*q)=LV ρ/w>1. Thus, where ID is an internal diameter for a tubing or replacement fluid line 416, then if ID=0.126", and V=0.2045 ml/in, for a high capacity scale having w=5 g, assuming ρ=1 g/ml, then for L(0.2045)(1)/5>1 it must be that L>25". That is, the non-metric portion of tubing L, which is the replacement fluid line 416, must be >25" in length to respond in time to stop the pump 202 so as to prevent the air from reaching the disposable kit 418.

Looking at two different examples of pump flow rates for a procedure, relatively low and relatively high, one could also determine the response time required, if given the other variables. Thus, if for example, the pump flow rate is 25 ml/min (0.417 ml/s) and the length L of the non-metric line 416 is 22", the response time, or time permitted between when a container would be empty and when air would begin to be pumped into the disposable kit 418, would be represented by tr=LV/q=22*0.2045/0.417≈11 seconds. Similarly, if for example, the pump flow rate is 80 ml/min (1.333 ml/s) and the other variables remain the same, the response time would be represented by tr=LV/q=22*0.2045/1.333≈4 seconds.

Further, to try to capture the moment at which the first fluid supply container 204 empties it is desired to identify the point in time at which the slope of the scale time trace changes to 0, or surpasses a defined threshold. Calculating the scale slope must rely on a discrete backward difference formula. Given that the minimum resolution of the scale 402 is w grams, the minimum time over which the discrete difference stencil must be applied is >w/ρq. Thus, for the lower example flow rate of 25 ml/min (0.417 ml/s) and assuming ρ1 g/ml, and a scale resolution of w=5 g, the difference stencil must cover at least 5/(1*0.417)≈11 seconds. For the higher example flow rate of 80 ml/min (1.333 ml/s) and assuming ρ1 g/ml, and a scale resolution of w=5 g, the difference stencil must cover at least 5/(1*0.417)≈4 seconds. Thus, the sampling rates for the scale must be suitable to avoid air ingestion, as an alternative, a longer time interval would be available for a non-metric replacement fluid line 416 having a longer length L.

In accordance with one aspect of the disclosure, in order to confirm that the first fluid supply container is, in fact, "empty," and is not simply in a low flow rate condition due to, e.g., the high viscosity of the fluid in the container, to poor spike performance, or to improper loading of the fluid container (any one of which could result in a "false switching" of containers), the weight of the container must also be below a pre-established threshold weight, $W_{th}$ in graph 410, when the low flow rate condition, indicated by line 412 occurs. In one non-limiting example, a pre-established threshold weight of approximately 390 g may be selected, if a therapeutic plasma exchange is being performed, with albumin as the replacement fluid. This is suitable for fluid containers of both 500 ml and 250 ml of albumin, as an empty 500 ml bottle weighs approximately 316 g, while a full 250 ml bottle weights approximately 460 g. When both the low flow rate and a container weight below the pre-established threshold weight are detected, pumping from the "empty" container (204) will cease and, if appropriate, pumping from a second replacement fluid container (205) will commence.

In another aspect of the disclosure, by additionally monitoring the weight(s) of the replacement fluid containers, the system notifies the operator if the system detects a low flow scenario within a predetermined time after a switch of pumping from a first container to pumping from a second container, or a low weight, e.g. 45 grams, is detected on one or both of the scales for the fluid containers (indicating that no replacement fluid container is present). This permits the operator to take remedial actions to ensure that fluid flow continues uninterrupted, and avoid potential complication resulting from air entering the apheresis kit.

As illustrated in FIG. 2, the determination that a container is empty is based on a weight as measured by the scales 206, 207. However, other means could be used for determining this empty condition, such as optical, ultrasonic, or capacitance sensors, all as well known in the art. In a preferred example, the system notifies the operator with a visual and/or audible alarm in response to detection of any of the above-described scenarios, and such an alarm would be given if the scenario is detected less than, e.g., 15 seconds after a switch from one container to another container has occurred.

It is also desirable to accurately track the accumulated volume of fluid that is returned to the patient during the exchange procedure to ensure that it is either substantially equal to the amount of fluid that is removed or substantially equal to the programmed endpoint for desired fluid balance. This is typically determined based on the change in weight of the fluid containers during the exchange procedure. With reference to FIG. 2, the weight measured by the scales 206, 207 associated with the fluid containers 204, 205 does not include the volume of the fluid contained in tubing segment leading to the valve (210 or 211) that is pumped prior to the system detecting an empty container. Thus, in accordance with the systems and methods disclosed herein, the accumulated weight of the returned fluid is automatically increased by the system each time there is a switch between containers by an amount corresponding to the amount of replacement fluid in the tubing segment leading to the valve(s). As can be appreciated, this value is dependent upon the particular style or model of tubing kit utilized. For example, in the therapeutic plasma exchange kits used with the Amicus® separator referenced above the volume of the tubing segment has been determined empirically to be approximately 11 ml, and this amount is added to the accumulated replaced volume each time the system automatically switches between fluid containers. Of course, it will be appreciated that the added volume may differ depending on the instrument, kit and/or procedure employed.

While particular embodiments have been shown and described, it will be obvious to those skilled in the art that changes and modifications may be made therein without departing from the disclosure in its broader aspects.

What is claimed is:

1. A blood processing apparatus configured to process blood in a disposable fluid flow system that may be associated therewith, the disposable fluid flow system having at least a first fluid supply container and a second fluid supply container, each containing a fluid to be reinfused into a patient, the apparatus comprising:
a first scale for measuring a weight of the first fluid supply container and providing a first output signal indicative of the measured weight of the first fluid supply container;
a second scale for measuring a weight of the second fluid supply container and providing a second output signal indicative of the measured weight of the second fluid supply container;
a pump for pumping fluid from the first and second fluid supply containers for reinfusion into the patient;
a first valve in fluid communication between the first fluid supply container and the pump, the first valve normally in an open condition;
a second valve in fluid communication between the second fluid supply container and the pump, the second valve normally in a closed condition;
a controller configured to receive the first output signal from the first scale, to determine a rate of change in weight of the first fluid supply container, to determine that the first fluid supply container is empty when the rate of change becoming substantially zero occurs simultaneously with the first fluid supply container weight being below a first pre-established threshold that is greater than a weight of the first fluid supply container when empty; to cause the pump to cease pumping upon determining that the first fluid supply container is empty, to cause the second valve to move to an open condition and to cause the first valve to move to a closed condition, to activate the pump to begin pumping fluid from the second fluid supply container, and to provide notification when a ratio of the rate of change in weight to a volume pumped is less than a predetermined value for the second fluid supply container occurs simultaneously with less than a predetermined time elapsing after the pump begins pumping fluid from the second fluid supply container.

2. The blood processing apparatus of claim 1 wherein the pump operates in a first direction when pumping fluid from the first fluid supply container and the pump operates in a second direction when pumping fluid from the second fluid supply container.

3. The blood processing apparatus of claim 1 wherein the controller is configured to receive the second output signal from the second scale, to determine the rate of change in weight of the second fluid supply container, and to determine that the second fluid supply container is empty when the rate of change becoming substantially zero occurs simultaneously with the second fluid supply container weight being below a second pre-established threshold that is greater than the weight of the second fluid supply container when empty.

4. The blood processing apparatus of claim 1 wherein the first scale measures the weight of the first fluid supply container over pump-unit intervals and the controller is configured to compare a weight change measured by the first scale for each pump-unit interval to a volume pumped during the pump-unit intervals.

5. The blood processing apparatus of claim 4 wherein the controller is configured to indicate the first fluid supply container is empty if the ratio of the weight change to the volume pumped is less than a predetermined value for two consecutive pump-unit intervals.

6. The blood processing apparatus of claim 1 wherein the fixed, constant amount by which the controller increases the accumulated volume corresponds to a first volume of a first tubing segment leading from the first fluid supply container to the first valve or to a second volume of a second tubing segment leading from the second fluid supply container to the second valve.

7. The blood processing apparatus of claim 1 wherein the controller is further configured to track an accumulated volume of fluid pumped from the first fluid supply container based on the change of weight of the first fluid supply container, and to increase the accumulated volume by a fixed, constant amount for each time the pumping switches between the first and second fluid supply containers.

8. A blood processing apparatus configured to process blood in a selected one of a plurality of differently-configured disposable fluid flow systems that may be associated therewith, each fluid flow system having at least a first fluid supply container with a first tubing segment connected thereto and a second fluid supply container with a second tubing segment connected thereto, the apparatus comprising:
a first scale for measuring a weight of the first fluid supply container of the selected one of the plurality of differently-configured disposable fluid flow systems and providing a first output signal indicative of the measured weight of the first fluid supply container;
a second scale for measuring a weight of the second fluid supply container of the selected one of the plurality of differently-configured disposable fluid flow systems and providing a second output signal indicative of the measured weight of the second fluid supply container;
a pump for pumping fluid from the first fluid supply container;
a first valve in fluid communication between the first fluid supply container and the pump, the first valve normally in an open condition;

the first tubing segment connected to the first supply container leading to the first valve, the first scale being configured so as not to measure the weight of the first tubing segment when measuring the weight of the first fluid supply container;

a second valve in fluid communication between the second fluid supply container and the pump, the second valve normally in a closed condition;

the second tubing segment connected to the second supply container leading to the second valve, the second scale being configured so as not to measure the weight of the second tubing segment when measuring the weight of the second fluid supply container;

a controller configured to receive the first output signal from the first scale, and to determine a rate of change in weight of the first fluid supply container, the controller further configured to determine that the first fluid supply container is empty when a ratio of the rate of change in weight of the first fluid supply container to a rate of fluid flow from the pump being less than a predetermined value occurs simultaneously with the weight of the first fluid supply container being less than a first pre-established threshold; to cause the pump to cease pumping upon determining that the first fluid supply container is empty; to cause the second valve to move to an open condition and to cause the first valve to move to a closed condition; to then activate the pump to begin pumping fluid from the second fluid supply container; to provide notification when the ratio of the rate of change in weight to a volume pumped is less than a predetermined value for the second fluid supply container occurs simultaneously with less than a predetermined time elapsing after the pump begins pumping fluid from the second fluid supply container; to track an accumulated volume of fluid pumped from the first fluid supply container based on the change of weight of the first fluid supply container; and to increase the accumulated volume by a fixed, constant amount specific to the selected one of the plurality of differently-configured disposable fluid flow systems associated with the blood processing apparatus corresponding to a first volume of the first tubing segment leading to the first valve or to a second volume of the second tubing segment leading to the second valve for each time the pumping switches between the first and second fluid supply containers.

9. A method of processing blood in a disposable fluid flow system associated with a blood processing apparatus, the method comprising:

providing a first fluid supply container of the disposable fluid flow system adapted to be in communication with a patient when a first valve is in an open condition;

providing a second fluid supply container of the disposable fluid flow systems adapted to be in communication with the patient when a second valve is in an open condition;

monitoring a weight of the first fluid supply container while it is being emptied by a pump that is pumping fluid from the first fluid supply container into the patient;

establishing a first threshold weight for the first fluid supply container that is greater than a weight of the first fluid supply container when empty;

determining a rate of change of the weight of the first fluid supply container;

determining when the rate of change of the weight of the first fluid supply container becomes substantially zero simultaneously with the weight of the first fluid supply container being less than the first threshold weight;

stopping the operation of the pump and moving the first valve to a closed condition when the rate of change of the weight of the first fluid supply container is determined to be substantially zero and the weight of the first fluid supply container is less than the first threshold weight and moving the second valve to an open condition; and providing notification when a ratio of the rate of change of the weight to a volume pumped is less than a predetermined value for the second fluid supply container occurs simultaneously with less than a predetermined time elapsing after the pump begins pumping fluid from the second fluid supply container.

10. The method of claim 9 further comprising:

measuring the weight of the second fluid supply container while it is being emptied by the pump that is pumping fluid from the second fluid supply container into the patient;

establishing a second threshold weight for the second fluid supply container that is greater than a weight of the second fluid supply container when empty;

determining a rate of change of the weight of the second fluid supply container;

determining when the rate of change of the weight of the second fluid supply container becomes substantially zero simultaneously with the weight of the second fluid supply container being less than the second threshold weight; and stopping the operation of the pump when the rate of change of the weight of the second fluid supply container is determined to be substantially zero and the weight of the second fluid supply container is less than the second threshold weight.

11. The method of claim 9 further comprising tracking an accumulated volume of fluid pumped from the first and second fluid supply containers based on the change of weight of the fluid supply containers and increasing the accumulated volume by a fixed, constant amount corresponding to a first volume of a first tubing segment leading from the first fluid supply container to the first valve or to a second volume of a second tubing segment leading from the second fluid supply container to the second valve for each time the pumping switches between the first and second fluid supply containers.

* * * * *